United States Patent
Azria et al.

(10) Patent No.: US 7,569,539 B2
(45) Date of Patent: Aug. 4, 2009

(54) ORAL ADMINISTRATION OF CALCITONIN

(75) Inventors: Moise Azria, Basel (CH); Simon D Bateman, Randolph, NJ (US); James F Mcleod, Morristown, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 11/805,748

(22) Filed: May 24, 2007

(65) Prior Publication Data

US 2007/0232524 A1  Oct. 4, 2007

Related U.S. Application Data

(63) Continuation of application No. 10/523,421, filed as application No. PCT/EP03/08498 on Jul. 31, 2003, now abandoned.

(60) Provisional application No. 60/400,139, filed on Aug. 1, 2002.

(51) Int. Cl.
*A61K 38/00* (2006.01)
*A61K 38/23* (2006.01)
*C07K 14/00* (2006.01)
*C07K 14/585* (2006.01)

(52) U.S. Cl. .............................. 514/2; 514/12; 530/300; 530/307

(58) Field of Classification Search ........................ None
See application file for complete search history.

(56) References Cited

U.S. PATENT DOCUMENTS

| | | | | |
|---|---|---|---|---|
| 5,629,020 | A  * | 5/1997 | Leone-Bay et al. | 424/489 |
| 7,049,283 | B2 | 5/2006 | Ault et al. | 514/2 |
| 2002/0065255 | A1 | 5/2002 | Bay et al. | 514/166 |
| 2002/0123459 | A1* | 9/2002 | Ault et al. | 514/2 |

FOREIGN PATENT DOCUMENTS

| | | |
|---|---|---|
| WO | 00/59480 | 10/2000 |
| WO | 02/45754 | 6/2002 |

OTHER PUBLICATIONS

Fortical Nasal Spray for Osteoporosis Launched, from http://goliath.ecnext.com/coms2/gi_0199-4702616/FORTICAL-NASAL-SPRAY-FOR-OSTEOPOROSI, Oct. 1, 2005, pp. 1-3. Accessed May 14, 2009.*

* cited by examiner

*Primary Examiner*—Cecilia Tsang
*Assistant Examiner*—Julie Ha
(74) *Attorney, Agent, or Firm*—Leslie Fischer; Cozette M. McAvoy

(57) ABSTRACT

Disclosed is a particular method of orally administering pharmaceutical compositions comprising calcitonin in combination with oral delivery agents, prior to the consumption of food in humans, and a method of treatment of disorders responsive to the action of calcitonin employing such method of administration; also oral calcitonin pharmaceutical compositions with particular ratios of the amount of oral delivery agent to the amount of calcitonin.

7 Claims, No Drawings

ORAL ADMINISTRATION OF CALCITONIN

This is a continuation of application Ser. No. 10/523,421 filed on Jul. 28, 2005, which is National Stage of International Application Ser. No. PCT/EP03/08498 filed on Jul. 31, 2003, which claims benefit of U.S. provisional Application No. 60/400,139 filed on Aug. 1, 2002 the entire disclosures of which are hereby incorporated by reference.

FIELD OF THE INVENTION

This invention relates to orally effective pharmaceutical compositions of calcitonin, the administration thereof and treatment of disorders responsive to the action of calcitonin therewith in humans.

BACKGROUND OF THE INVENTION

U.S. Pat. Nos. 5,773,647 and 5,866,536, as well as International Application WO 00/59863 disclose pharmaceutical compositions for the oral delivery of calcitonin using modified amino acids as oral delivery agents. Said documents are incorporated herein by reference. Oral delivery agents disclosed include N-(5-chlorosalicyloyl)8-aminocaprylic acid (5-CNAC), N-10-[2-hydroxybenzoyl]aminodecanoic acid (SNAD) and N-(8-[2-hydroxybenzoyl]amino)caprylic acid (SNAC), disodium salts and hydrates and solvates thereof.

SUMMARY OF THE INVENTION

The present invention is directed to a particular method of orally administering pharmaceutical compositions comprising calcitonin in combination with one or more oral delivery agents, i.e., prior to the consumption of food in humans, and method of treatment of disorders responsive to the action of calcitonin employing such method of administration; also oral solid pharmaceutical compositions with particular ratios of the amount of oral delivery agent to the amount of calcitonin in which the amount of oral delivery agent is decreased.

DETAILED DESCRIPTION OF THE INVENTION

Particularly, the present invention is directed to treatment of disorders responsive to the action of calcitonin, which comprises the oral administration to a human host of a pharmaceutical composition comprising calcitonin and an oral delivery agent, said oral administration being in the absence of food, advantageously a short interval prior to the consumption of food, for instance, a short interval before a meal, so as to enhance the oral bioavailability of calcitonin.

Disorders responsive to the action of calcitonin are, e.g., Paget's disease, hypercalcemia and osteoporosis.

The term "about" as used herein denotes both the actual numbers of values cited, as well as a range falling within up to 10% below and above the cited numbers or values.

As used herein, "calcitonin" refers to a class of pharmacological agents used for the treatment of, e.g., Paget's disease, hypercalcemia and osteoporosis, including natural, synthetic or recombinant human, salmon, pig or eel calcitonin.

Preferred is salmon calcitonin (sCT). The calcitonins are commercially available or may be synthesized by known methods. A typical human dose of sCT is 100 IU (0.018 mg) when administered by injection.

The appropriate oral human dosage will vary depending, e.g., on the age of the subject, the oral formulation and the nature and severity of the condition to be treated. An oral human dose of sCT is typically in the range of about 0.05-5 mg, preferably about 0.1-2.5 mg, when administered in combination with an oral delivery agent.

The oral dosage will also vary depending on the delivery agent and the actual formulation involved.

Suitable oral delivery agents are those described in U.S. Pat. Nos. 5,773,647 and 5,866,536, as well as International Application WO 00/59863, the contents of which are incorporated herein by reference. Specific embodiments thereof are 5-CNAC, SNAD and SNAC, and the disodium salts and hydrates and solvates thereof, such as the ethanol solvates. The disodium salts, monohydrates and ethanol solvates are described in International Application WO 00/59863, including their preparation.

Preferred as oral delivery agent is 5-CNAC, particularly the disodium salt or the hydrate or solvate thereof, such as the ethanol solvate.

Typically, the hydrate or ethanol solvate of, e.g., the disodium salt of 5-CNAC contains about one molecule of water or ethanol per molecule of the oral delivery agent, thus being a monohydrate or monoethanol solvate.

Particularly preferred is 5-CNAC disodium salt, advantageously the monohydrate form thereof.

As used herein "5-CNAC" denotes N-(chlorosalicyloyl)-8-aminocaprylic acid. Unless denoted otherwise, the term "disodium salt" used in connection with 5-CNAC refers to the disodium salt in any form.

5-CNAC is described in U.S. Pat. No. 5,773,647, the contents of which are hereby incorporated by reference, and can be made by methods described therein. The sodium salts and alcohol solvates and hydrates thereof, along with methods for preparing them, are described in WO 00/59863, which is also incorporated herein by reference. Examples 2 and 7 of WO 00/59863 are directed, respectively, to 5-CNAC disodium salt monohydrate and 5-CNAC disodium salt monoethanol solvate.

Surprisingly, it has now been found that the oral administration of a calcitonin formulation, preferably a solid calcitonin formulation comprising calcitonin and an oral delivery agent, at a short interval prior to a meal greatly increases the oral absorption and the systemic bioavailability of calcitonin in comparison to administration with a meal.

The short interval for administration prior to a meal is up to 2 hours, advantageously about 5 minutes to 1 hour, preferably about 5 to 30 minutes, most preferably about 5 to 15 minutes, and as little as about 2-5 minutes or just prior to a meal.

A meal represents particularly a standard meal, namely breakfast, lunch or dinner.

The increase in oral absorption and systemic bioavailability of calcitonin is determined by measuring the plasma concentration of calcitonin achieved after administration of the drug at various intervals prior to a meal and at mealtime. Typically, the plasma concentration is measured at predetermined periods after the administration of the drug so as to determine the maximum plasma concentration ($C_{max}$) and the total amount absorbed as determined by the area under the curve (AUC).

Illustrative of the invention, about a 5-fold increase ($C_{max}$ and AUC) in oral absorption is achieved by administering to human subject a tablet formulation comprising 1 mg of sCT and the disodium salt of 5-CNAC (in an amount equivalent to 200 mg of 5-CNAC) when such formulation is administered in the range of 5 to 60 minutes prior to a meal, instead of with a meal.

Therefore, a particular aspect of the invention is a method of enhancing and maximizing the oral absorption and systemic bioavailability of calcitonin in humans from a formulation comprising calcitonin and an oral delivery agent by administering a said formulation to a human host in need thereof at a short interval prior to the consumption of food, from about 5 minutes to 2 hours before a meal, and preferably as indicated hereinabove.

In view of the increased bioavailability, another aspect of the invention involves a method of reducing the amount of calcitonin in a formulation comprising calcitonin and an orally delivery agent to be orally administered to a human host in need thereof, which method comprises the administration of said formulation at a short interval prior to the consumption of food, preferably about 5 minutes to 2 hours before a meal and preferably as further indicated herein.

The amount of oral delivery agent relative to the amount of calcitonin in the formulations depends on the nature of the delivery agent and is generally in the range of about 10 to about 1,000:1, preferably in the range of about 10 to about 500:1, most preferably about 10 to about 250:1. For example, the ratio by weight of the amount of 5-CNAC disodium salt (expressed as corresponding amount of 5-CNAC free acid) to the amount of sCT is in the range of about 10 to about 250:1, preferably about 25 to about 100:1 when the disodium salt of 5-CNAC is used as an oral delivery agent.

A particular aspect of the invention is directed to an oral pharmaceutical composition comprising:

a) an oral delivery agent being the disodium salt of 5-CNAC, SNAD or SNAC, or a hydrate or solvate of a said disodium salt; and b) about 0.1-2.5 mg of calcitonin; in which the ratio of the amount of the oral delivery agent, expressed as the corresponding amount of free acid, to the amount of calcitonin is in the range of about 10 to about 250:1 by weight.

Preferred is an oral solid pharmaceutical composition, comprising 5-CNAC disodium salt or a hydrate thereof and about 0.1-2.5 mg of sCT in which the ratio of the amount of the oral delivery agent to the amount of calcitonin as defined above is in the range of about 10 to about 200:1 by weight.

Further preferred is an oral solid pharmaceutical compositions in which the ratio as defined above is about 25 to about 100:1 by weight.

A particular aspect of the invention is directed to a kit comprising:

a) an oral pharmaceutical composition comprising calcitonin and an oral delivery agent being the disodium salt of N-(5-chlorosalicyloyl)-8-aminocaprylic acid, N-(10-[2-hydroxybenzoyl]aminodecanoic acid or N-(8-[2-hydroxybenzoyl]amino)caprylic acid, or a hydrate or solvate of a said disodium salt; and b) written instructions which instructions provide that said oral pharmaceutical composition may be taken prior to the consumption of food.

Preferred is a kit comprising next to the written instructions as mentioned above, about 0.1-2.5 mg of calcitonin; in which the ratio of the amount of the oral delivery agent, expressed as the corresponding amount of free acid, to the amount of calcitonin is in the range of about 10 to about 250:1 by weight. More preferred is a kit comprising 5-CNAC disodium salt or a hydrate thereof and about 0.1-2.5 mg of sCT in which the ratio of the amount of the oral delivery agent to the amount of calcitonin as defined above is in the range of about 10 to about 200:1 by weight.

The solid pharmaceutical compositions used for oral administration may be in form of a capsule (including a soft-gel capsule), tablet, caplet or other solid oral dosage form, all of which can be prepared by methods well-known in the art.

Preferably, the solid pharmaceutical compositions also contain a crospovidone and/or povidone, advantageously crospovidone.

The crospovidone can be any crospovidone. Crospovidone is a synthetic cross-linked homopolymer of N-vinyl-2-pyrrolidone, also called 1-ethenyl-2-pyrrolidinone, having a molecular weight of 1,000,000 or more. Commercially available crospovidones include Polyplasdone XL, Polyplasdone XL-10, Polyplasdone INF-10 available from ISP, Kollidon CL, available from BASF Corporation. The preferred crospovidone is Polyplasdone XL.

Povidone is a synthetic polymer consisting of linear 1-vinyl-2-pyrrolidinone groups having a molecular weight generally between 2,500 and 3,000,000. Commercially available povidones include Kollidon K-30, Kollidon K-90F available from BASF Corporation and Plasdone K-30 and Plasdone K-29/32, available from ISP.

The crospovidones and povidones are commercially available. Alternatively, they may be synthesized by known processes.

The crospovidone, povidone or combination thereof is generally present in the compositions in an amount of from 0.5-50% by weight relative to the total weight of the overall pharmaceutical composition, preferably an amount of from 2-25%, more preferably 5-20% by weight relative to the total weight of the pharmaceutical composition.

A particular aspect of the invention is a pharmaceutical composition for oral administration of sCT to humans which comprises 5-CNAC disodium salt, calcitonin and crospovidone, the weight ratio of 5-CNAC as free acid to sCT being in the range of about 10 to about 200:1.

Alternatively, the solid pharmaceutical compositions may contain croscarmellose sodium (AC-DI-SOL®) and/or colloidal silicon dioxide (CAB-O-SIL®).

Also, the calcitonin and oral delivery agent may be used in the form of a colyophilized mixture, e.g., of sCT and the disodium salt of 5-CNAC.

The compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant, such as magnesium stearate, a flow aid, a compression aid, a solubilizer, an excipient, a diluent, such as microcrystalline cellulose, e.g., Avicel PH 102 supplied by FMC Corporation, or any combination thereof. Other additives may include phosphate buffer salts, citric acid, glycols and other dispersing agents.

The compositions are administered orally, typically once a day, for instance, before breakfast, to systemically deliver a therapeutically effective amount of calcitonin.

The solid pharmaceutical compositions of the instant invention can be prepared by conventional methods, e.g., by blending a mixture of the active agent or active agents, the delivery agent and other ingredients, and filling into capsules or, instead of filling into capsules, compression-molding to give tablets. In addition, a solid dispersion may be formed by known methods followed by further processing to form a tablet or capsule.

Typical pharmaceutical formulations are given in the examples. In the examples, 5-CNAC denotes N-(5-chlorosalicyloyl-8-aminocaprylic acid. When its disodium salt is an ingredient in the examples, a corresponding amount of the disodium salt monohydrate is actually used. The amount given in the examples is the amount of the anhydrous disodium salt.

EXAMPLE 1

0.52 g of sCT, pre-screened through a 40-mesh screen, 120 g of 5-CNAC disodium salt, pre-screened through a 35-mesh screen, and 20 g of Polyplasdone XL (crospovidone, NF) is combined in a 500 mL jar and is mixed using a Turbula mixer for 2 minutes at a speed of 46 RPM. An additional 125.4 g of 5-CNAC disodium salt, pre-screened through a 35-mesh screen, and 32.5 g of Avicel PH 102 is added to the jar and is mixed for a period of 8 minutes at a speed of 46 RPM. A further 32.5 g of Avicel is added to the jar and is mixed for 5 minutes at a speed of 46 RPM. 4.0 g of magnesium stearate is screened into the jar using a 35-mesh screen and is blended for 1 minute at a speed of 46 RPM. The final blend is compressed into tablets using a Manesty B3B tablet press. The tablet weight is approximately 400 mg.

EXAMPLE 2

A mixture of 14 g of the disodium salt of 5-CNAC and 0.56 g of CAB-O-SIL is sieved through a 40-mesh screen. 0.3 g of the 5-CNAC disodium/CAB-O-SIL mixture, 0.028 g sCT, pre-screened through a 40-mesh screen, and 0.56 g of AC-DI-SOL, pre-screened through a 30-mesh screen are combined in a 1 quart V-blender shell. The mixture is blended for two minutes. Approximately 14.3 g of the 5-CNAC disodium/CAB-O-SIL mixture is added geometrically to the V-blender shell and mixed for 2 minutes after each addition (approximately 0.8, 1.7, 3.2 and 8.6 g are added successively). 12.43 g of Avicel PH 102 and 0.42 g of magnesium stearate, pre-screened through a 40-mesh screen are added to the V-blender shell and mixed for 5 minutes. The final blend is then screened through a 40-mesh screen and is compressed into tablets using, e.g., a Manesty F3 press. The tablet weights are approximately 400 mg.

EXAMPLE 3

0.1224 of sCT, pre-screened through a 40-mesh screen, 30 g of 5-CNAC disodium salt, pre-screened through a 35 mesh screen, and 4 g of AC-DI-SOL are placed in a 500 mL Pyrex® jar and are mixed using a Turbula mixer for 2 minutes at a speed of 46 RPM. An additional 31.35 g of 5-CNAC disodium salt, pre-screened through a 35-mesh screen, and 15 g of Avicel PH 102 are added to the jar and are mixed for a period of 8 minutes at a speed of 46 RPM. 2 g of CAB-O-SIL and 16.15 g of Avicel are combined and are screened through an 18-mesh screen. The CAB-O-SIL/Avicel mixture is added to the jar and is mixed for 5 minutes at a speed of 46 RPM. 1.5 g of magnesium stearate is screened into the jar using a 35-mesh screen and is blended for 2 minutes at a speed of 46 RPM. The final blend is compressed into tablets using a Manesty B3B tablet press. The tablet weights are approximately 400 mg.

EXAMPLE 4

18 kg of water for injection and 0.16 kg of sodium hydroxide, NF, are added to a vessel and mixed until dissolved. 0.800 kg of the free acid of 5-CNAC is added to the vessel and stirred at 400-600 RPM for a minimum of 10 minutes. The pH of the vessel is adjusted to approximately 8.5 using 10 N sodium hydroxide. The vessel is stirred for a minimum of 10 minutes after each addition of 10 N sodium hydroxide. The 10 N sodium hydroxide is prepared by adding 40 g of sodium hydroxide, NF, to 100 mL of water for injection. The final weight of the compounded solution is adjusted to 20.320 kg by the addition water for injection (density 1.016). The vessel is stirred at 400-600 RPM for a minimum of 30 minutes. The compounded solution is filtered into another vessel using a peristaltic pump, silicone tubing, and a DuraPore 0.45 μm MPHL membrane capsule filter. A phosphate buffer solution is prepared by adding 13.8 g of monosodium phosphate monohydrate, USP to 900 g of water for injection and adjusting to a pH of 4.0 utilizing a 1.0 N phosphoric acid solution. The phosphoric acid solution is prepared by adding 0.96 g of phosphoric acid, NF, to 25 mL of water for injection. The final weight of the phosphate buffer solution is adjusted to 1007 g (density 1.007) using water for injection and is stirred for 5 minutes.

A buffered sCT solution is prepared by adding 1.6 g of sCT to 660-g of the phosphate buffer solution. The final weight of the solution is adjusted to a final weight of 806.4 g (density 1.008) using the phosphate buffer solution and mixed for a minimum of 5 minutes at a speed of 250 RPM or less.

0.800 kg of the buffered sCT-solution is added dropwise to 20 kg of 5-CNAC solution with constant mixing at a speed of 250 RPM or less for a minimum of 5 minutes. Approximately 0.75 L of the sCT/5-CNAC solution is filled into stainless steel lyophilization trays (30.5×30.5 cm) for a final solution depth of 0.8-0.9 cm. Approximately 29 trays are filled with 21.75 L of sCT/5-CNAC solution. The trays are placed into an Edwards freeze dryer and lyophilized according to the following procedure:

1. When trays are loaded and the Reeze dryer is sealed, the shelves are cooled at a rate of 1° C. per minute.
2. Once the shelf temperature reaches −45° C., the shelf temperature is maintained at −45° C. for a minimum of 120 minutes.
3. The condenser is cooled to −50° C. or below.
4. The chamber is evacuated and when a vacuum of 300 microns is maintained, the shelf temperature is raised to −30° C. at a rate of 1° C. per minute.
5. The shelf temperature is maintained at −30° C. for 180 minutes.
6. The pressure in the chamber is reduced to 200 microns and when a vacuum of 200 microns is maintained, the shelf temperature is raised to −20° C. at a rate of 1° C. per minute.
7. The shelf temperature is maintained at −20° C. for 200 minutes.
8. The shelf temperature is raised to −10° C. at a rate of 1° C. per minute.
9. The shelf temperature is maintained at −10° C. for 360 minutes.
10. The shelf temperature is raised to 0° C. at a rate of 1° C. per-minute.
11. The shelf temperature is maintained at 0° C. for 720 minutes.
12. The pressure in the chamber is reduced to 100 microns and when a vacuum of 100 microns is maintained, the shelf temperature is raised to +10° C. at a rate of 1° C. per minute.
13. The shelf temperature is maintained at +10° C. for 540 minutes.
14. The shelf temperature is raised to +25° C. at a rate of 1° C. per minute.
15. The shelf temperature is maintained at +25° C. for 440 minutes.
16. The vacuum is released and trays are unloaded.

The colyophilized sCT/5-CNAC is removed from the trays and stored in polyethylene and foil bags under refrigeration. Approximately 400 mg of colyophilized material is filled into capsules (size M) for administration.

EXAMPLE 5

The following tablet formulations are prepared similarly to Example 1.

| Ingredients | Amount of sCT per tablet | | | |
|---|---|---|---|---|
| | 0.15 mg | 0.4 mg | 1 mg | 2.5 mg |
| Salmon calcitonin | 0.15 mg | 0.4 mg | 1 mg | 2.5 mg |
| 5-CNAC disodium salt* | 228 mg | 228 mg | 228 mg | 228 mg |
| Microcrystalline cellulose, NF (Avicel PH-102) | 147.85 mg | 147.6 mg | 147 mg | 145.5 mg |
| Crospovidone, NF | 20 mg | 20 mg | 20 mg | 20 mg |
| Magnesium stearate, NF | 4 mg | 4 mg | 4 mg | 4 mg |
| Total | 400 mg | 400 mg | 400 mg | 400 mg |

*The material used is 5-CNAC disodium salt monohydrate in an amount corresponding to 228 mg of anhydrous 5-CNAC disodium salt, which amount is equivalent to 200 mg of 5-CNAC free acid.

EXAMPLE 6

Similarly prepared to Example 1 are tablets containing 0.5 or 1 mg of sCT and 5-CNAC disodium salt in an amount corresponding to 25, 50, 100, 200 and 400 mg of 5-CNAC free acid.

EXAMPLE 7

The effect of administration of a tablet formulation of sCT in combination with 5-CNAC disodium salt at various time intervals relative to meals is measured in human subjects.

The tablet formulation employed is a formulation according to Example 5, comprising 1 mg sCT and 5-CNAC disodium salt in an amount corresponding to 200 ng of 5-CNAC.

The study employs a seven-period, randomized, open-label, balanced Latin-square, crossover design. Twenty-one human healthy adult subjects (7 males, 7 pre-menopausal females and 7 post-menopausal females), between the ages of 18 and 65 years of age are involved. Pre- and post-menopausal females are matched for height (±0.5 cm) and weight (±8%).

The study consists of a screening period (−21 to −2 days prior to dosing), a baseline period (24-hour period prior to dosing, or day −1), and a treatment period comprised of seven daily single-dose administrations. Subjects are instructed to fast for at least 8 hours prior to undergoing screening evaluations so that blood samples can be drawn for bioanalytical testing. At baseline, subjects are admitted to the study center at least 12 hours prior to dosing and remain domiciled until study completion (one day following the final dose of study drug, or study day 8). The interdose interval between each treatment will be approximately 24 hours. Subjects are randomized according to the treatment allocation schedule to receive a single oral dose under either fasted or fed conditions. Under fed conditions, meal times vary relative to a fixed dosing time, in order to assess the effect of varying meal and dose intervals on drug pharmacokinetics.

During the treatment period, subjects fast overnight for a minimum of 10 hours prior to dosing, except when the specified treatment condition requires a meal to be served pre-dose. Dosing occurs between 9 and 10 AM for seven consecutive days. Meal times vary around a fixed dosing interval over a seven-day treatment period in order to determine optimal dosing times relative to food intake. Included is the administration of study drug under fasting conditions, which will serve as the reference condition to assess drug pharmacokinetics under varying meal and dose intervals, as well as study drug administration with meals, to determine the extent of food interaction.

The order in which subjects are initially dosed remains consistent throughout the study, so that the first subject dosed in period 1 remains the first subject dosed across all treatment conditions. Except where fasting is the specified treatment condition, subjects receive a standardized FDA (or equivalent) high-fat breakfast at a different time each day relative to dosing. Subjects whose treatment assignment is to fast, continue fasting for at least four hours post-dose, after which they may receive a standard meal at the specified time. Sampling for pharmacokinetic assessments are performed at scheduled intervals for up to 8 hours post-dose. If pharmacokinetic sampling times coincide with the start of a meal, sampling occurs first. Subjects are discharged from the study center one day following the final dose of study drug (day 8), after the completion of all safety evaluations.

Pharmacokinetic blood sampling is performed each day at the following timepoints (unless otherwise specified, when sampling times coincide with the start of a meal, sampling is done first): pre-dose (5 mL blood on each treatment day, lithium-heparin tubes to yield plasma), and then 5, 10, 15, 30, 45, 60, 90, 120, 180 and 240 minutes post-dose (3 mL blood), lithium-heparin tube to yield plasma). For treatment conditions B, C, D and E (see table below) one additional sample (3 mL) is obtained at 5 minutes after the start of the meal. For treatment condition E, the 10 minute sample also represents the 5-minute post-meal sample. For treatment B only, one additional sample is obtained at 15 minutes after the start of the meal (i.e., at 75 minutes post-dose).

All blood samples are taken by either direct venipuncture or an indwelling cannula inserted in a forearm vein, sCT samples are collected in lithium-heparin tubes.

Immediately after each tube of blood is drawn, it is inverted gently several times to ensure the mixing of tube contents, e.g., anti-coagulant, while avoiding prolonging sample contact with the rubber stopper. The tube is placed upright in a test tube rack surrounded by ice until centrifugation. Within 15 minutes, the sample is centrifuged between 3° C. and 5° C. for 10 minutes at approximately 3,000 g. All samples are frozen as soon as possible (but not later than 60 minutes from the time of venipuncture). The tubes are kept frozen at −70° C. or below pending analysis.

Immediately after centrifugation, at least 1.5 mL of plasma is transferred (except for pre-dose on each treatment day, when 2.5 mL of plasma is transferred) to a polypropylene screw-cap tube put on dry ice.

The sCT concentration is determined using a chemiluminescence-based immunoassay method; the LOQ is 2.5 pg/mL.

The results from each treatment group are averaged for each time point and plotted. The maximum mean plasma sCT concentration ($C_{max}$) and the AUC are determined and given in Table I.

TABLE I

Effect of meal administration on sCT bioavailability

| Treatment group | Time of administration | Mean AUC ± SD (pg · h/mL) | Mean $C_{max}$ ± SD (pg/mL) |
|---|---|---|---|
| A | After overnight fast | 66.3 ± 42.2 | 139.3 ± 74.3 |
| B | 1 hour pre-meal | 63.4 ± 37.9 | 135.9 ± 64.7 |
| C | 30 minutes pre-meal | 79.0 ± 79.3 | 161.7 ± 141.8 |
| D | 15 minutes pre-meal | 72.1 ± 45.1 | 161.9 ± 67.9 |
| E | 5 minutes pre-meal | 60.4 ± 67.4 | 149.5 ± 150.7 |
| F | With meal | 12.6 ± 18.5 | 24.0 ± 26.7 |
| G | 2.5 hours post-meal | 61.1 ± 114.2 | 79.8 ± 133.5 |

The results indicate that administration with a meal (Group F) leads to only negligible plasma levels of sCT. The maximum plasma levels are obtained in Groups C and D, in which the sCT/5-CNAC tablet formulation is administered either 15 or 30 minutes before a meal.

EXAMPLE 8

The oral bioavailability of sCT in human subjects administered 1 mg of sCT and 5-CNAC disodium salt in varying amounts, corresponding to either 25, 50, 100, 200 or 400 mg of 5-CNAC as free add, is determined.

Subjects are dosed daily as follows:

| Treatment group | No. of tablets | Contents per tablet sCT (mg) | *5-CNAC (mg) |
|---|---|---|---|
| A | 1 | 1 | 25 |
| B | 1 | 1 | 50 |
| C | 1 | 1 | 100 |
| D | 1 | 1 | 200 |
| E | 2 | 0.5 | 200 |

*The corresponding amount of 5-CNAC disodium salt monohydrate is used as the ingredient in the tablet formulations.

The tablets are prepared according to Examples 1 and 6. The tablet formulations are as follows:

| Ingredients | Treatment group A | B | C | D | E |
|---|---|---|---|---|---|
| Salmon calcitonin | 1 mg | 1 mg | 1 mg | 1 mg | 0.5 mg |
| 5-CNAC disodium salt* | 28.5 mg | 57 mg | 114 mg | 228 mg | 228 mg |
| Microcrystalline cellulose, NF (Avicel PH-102) | 17.5 mg | 36 mg | 73 mg | 147 mg | 147.5 mg |
| Crospovidone, NF | 2.5 mg | 5 mg | 10 mg | 20 mg | 20 mg |
| Magnesium stearate, NF | 0.5 mg | 1 mg | 2 mg | 4 mg | 4 mg |
| Total | 50 mg | 100 mg | 200 mg | 400 mg | 400 mg |

*The material used is 5-CNAC disodium salt monohydrate in an amount corresponding to the indicated amount of anhydrous 5-CNAC disodium salt, which amount is equivalent to 25, 50, 100 and 200 mg, respectively, of 5-CNAC free acid.

The study employs a two phase, seven-period, randomized, open-label, crossover design. A total of 15 healthy adult subjects between the ages of 18 and 50 years of age are involved. The study consists of a screening period (−2 to −21 days prior to dosing), a baseline period (the 24-hour period prior to dosing, or day −1), and treatment periods comprised of seven single-day, single-dose administrations. Subjects are instructed to fast for at least 8 hours prior to undergoing screening evaluations so that blood can be drawn for bioanalytical testing. At baseline, subjects are admitted to the study center at least 12 hours prior to dosing and remain domiciled until study-completion, one day following the final administration of study drug (day 8). The interdose interval between each treatment is approximately 24 hours.

During each treatment period, subjects fast overnight for a minimum of 1.0 hours prior to dosing and for 5 hours after dosing. Dosing occurs between 8 and 9 AM for seven consecutive days. The order in which subjects are initially dosed will remain consistent throughout the study, so that the first subject dosed in period 1 will remain the first subject dosed across all treatment conditions. Replacement subjects are assigned the same corresponding number and dosed in the same order.

Blood sampling and sCT concentration determination are carried out similarly to Example 7.

The results from each treatment group are averaged for each time point and plotted. The maximum mean plasma sCT concentration ($C_{max}$) and the AUC are determined and such are listed in Table II.

TABLE II

Effect of 5-CNAC ratio on sCT bioavailability

| Treatment group | 5-CNAC/sCT ratio* | Mean AUC ± SD (pg · h/mL) | Mean $C_{max}$ ± SD (pg · h/mL) |
|---|---|---|---|
| A | 25:1 | 62.4 ± 35.2 | 178.3 ± 93.6 |
| B | 50:1 | 83.7 ± 67.9 | 224.4 ± 150.1 |
| C | 100:1 | 42.1 ± 29.8 | 113.6 ± 67.1 |
| D | 200:1 | 116.9 ± 155.3 | 211.5 ± 210.4 |
| E | 400:1 | 91.6 ± 45.9 | 177.3 ± 62.8 |

*The ratio by weight of 5-CNAC free acid to sCT; the corresponding amount of 5-CNAC disodium salt monohydrate is actually used in the tablet formulations.

The data indicates that tablet formulations comprising sCT and 5-CNAC disodium salt in which the ratio of 5-CNAC to sCT is in the range of 25 to 400:1 result in comparable plasma levels of sCT.

The invention claimed is:

1. A method of administration which comprises administering orally to a human host at from about 15 minutes to 30 minutes prior to a meal, a pharmaceutical composition comprising calcitonin in combination with one or more oral delivery agents selected from the group consisting of N-(5-chlorosalicyloyl)-8-aminocaprylic acid, N-(10-[2-hydroxybenzoyl]aminodecanoic acid, N-(8-[2-hydroxybenzoyl]amino)caprylic acid, and disodium salts.

2. The method according to claim 1, wherein said pharmaceutical composition comprises about 0.1-2.5 mg of calcitonin.

3. The method according to claim 2, in which the ratio of the amount of the oral delivery agent, expressed as the corresponding amount of free acid, to the amount of calcitonin is in the range of about 10 to about 250:1 by weight.

4. The method according to claim 1, wherein the oral delivery agent is the disodium salt of N-(5-chlorosalicyloyl)-8-aminocaprylic acid.

5. The method according to claim 2, wherein the oral delivery agent is the disodium salt of N-(5-chlorosalicyloyl)-8-aminocaprylic acid.

6. A method of enhancing and maximizing the oral absorption and systemic bioavailability of calcitonin in a human comprising, orally administering to a human host at from about 15 minutes to 30 minutes prior to a meal a formulation comprising calcitonin in combination with one or more oral delivery agents selected from the group consisting of N-(5-chlorosalicyloyl)-8-aminocaprylic acid, N-(10-[2-hydroxybenzoyl]aminodecanoic acid, N-(8-[2-hydroxybenzoyl]amino)caprylic acid, and disodium salts.

7. A method of reducing the amount of calcitonin in an oral delivery formulation comprising, orally administering to a human host at from about 15 minutes to 30 minutes prior to a meal a formulation comprising calcitonin in combination with one or more oral delivery agents selected from the group consisting of N-(5-chlorosalicyloyl)-8-aminocaprylic acid, N-(10-[2-hydroxybenzoyl]aminodecanoic acid, N-(8-[2-hydroxybenzoyl]amino)caprylic acid, and disodium salts.

* * * * *

UNITED STATES PATENT AND TRADEMARK OFFICE
CERTIFICATE OF CORRECTION

PATENT NO. : 7,569,539 B2
APPLICATION NO. : 11/805748
DATED : August 4, 2009
INVENTOR(S) : Moise Azria et al.

It is certified that error appears in the above-identified patent and that said Letters Patent is hereby corrected as shown below:

Col. 10 line 54, after the word "salts", please insert the word --thereof--.

Col. 11 line 9, after the word "salts", please insert the word --thereof--.

Col. 12 line 8, after the word "salts", please insert the word --thereof--.

Signed and Sealed this

Twenty-third Day of February, 2010

David J. Kappos
*Director of the United States Patent and Trademark Office*